United States Patent [19]

Maahs et al.

[11] 4,297,505

[45] Oct. 27, 1981

[54] PROCESS FOR THE PREPARATION OF PENTACHLORO-3-BUTENOIC ACID ESTERS

[75] Inventors: Günther Maahs; Konrad Rombusch, both of Marl, Fed. Rep. of Germany

[73] Assignee: Chemische Werke Huels, Aktiengesellschaft, Marl, Fed. Rep. of Germany

[21] Appl. No.: 161,617

[22] Filed: Jun. 20, 1980

[30] Foreign Application Priority Data

Jun. 21, 1979 [DE] Fed. Rep. of Germany ....... 2925012

[51] Int. Cl.$^3$ ............................................. C07C 69/65
[52] U.S. Cl. .................................................... 560/219
[58] Field of Search ......................................... 560/219

[56] References Cited

PUBLICATIONS

Roedig, Alfred et al., *Justus Liebigs Annalen der Chemie*, vol. 600 (1956), pp. 1-11.
March, Jerry, "Advanced Organic Chemistry", 2nd Ed., pp. 341-342 (1979), Publ., McGraw-Hill.

*Primary Examiner*—Natalie Trousof
*Assistant Examiner*—L. Hendriksen
*Attorney, Agent, or Firm*—Millen & White

[57] ABSTRACT

A process for preparing a pentachloro-3-butenoic acid alkyl ester comprises reacting the corresponding 1-alkoxyheptachloro-3-butene with an aqueous solution of an alkali metal carbonate. In a preferred embodiment, the starting material 1-alkoxyheptachloro-3-butene is the solution obtained as the reaction product of the reaction of the corresponding 1-alkoxypentachloro-1,3-butadiene with chlorine.

11 Claims, No Drawings

PROCESS FOR THE PREPARATION OF PENTACHLORO-3-BUTENOIC ACID ESTERS

BACKGROUND OF THE INVENTION

It is conventional to produce pentachloro-3-butenoic acid esters by adding two chlorine atoms to 1-ethoxypentachloro-1,3-butadiene; splitting off chloroethane from the thus-formed 1-ethoxyheptachloro-3-butene by heating; and reacting the thus obtained pentachloro-3-butenoic acid chloride with an alcohol [Liebigs Ann. Chem. 600:1 (1956)]. However, this process has considerable disadvantages. For instance, when producing the starting material 1-ethoxypentachloro-1,3-butadiene from hexachloro-1,3-butadiene (conversion about 60%, selectivity about 65%), by-products—in most cases higher-boiling compounds—are produced to a considerable extent. On the one hand, in attempting to separate these by-products and the unreacted hexachloro-1,3-butadiene by distillation on an industrial scale (in the presence of iron-containing vessel materials), a considerable portion of the 1-ethoxypentachloro-1,3-butadiene is decomposed. On the other hand, if this separation is not performed and the step of splitting off chloroethane from the 1-ethoxyheptachloro-3-butene is conducted using the crude product still containing hexachloro-1,3-butadiene and by-products, the yield of pentachloro-3-butenoic acid chloride is drastically reduced (see Comparative Example A).

It is furthermore known to prepare pentachloro-3-butenoic acid esters by adding two chlorine atoms to tetrachlorocyclobutenone and reacting the thus-produced pentachloro-3-butenoic acid chloride with an alcohol (DOS [German Unexamined Laid-Open Application] No. 2,754,670 and corresponding to U.S. Pat. No. 4,175,095). This process, however, has attendant problems with regard to the preparation of the starting compound, using tetrachlorocyclobutenone.

This is evidenced by the results of the attempt to split off chloroethane from 1-ethoxypentachloro-1,3-butadiene to obtain tetrachlorocyclobutenone (German Pat. Nos. 1,206,433 and 1,271,111) on an industrial scale. Although the reaction takes place satisfactorily on a laboratory scale, only small yields are produced. For another tetrachlorocyclobutenone preparation, the starting compound, 3, 3, 4, 4,-tetrafluoro-2-chloro-1-methoxy-1cyclobutene (Chem. Ber. [Chemical Reports] 99:1966 [1970]), is accessible only with difficulty. Furthermore, tetrachlorocyclobutenone can also be obtained in a smooth reaction from hexachlorocyclobutene according to a process not yet part of the state of the art (German patent application P No. 28 10 398.2 and corresponding to U.S. application Ser. No. 019,105 filed on Mar. 9, 1979); however, the production of the latter compound is burdened by high initial investment costs occasioned by a requisite very expensive distillation.

As can be seen, there is presently no fully satisfactory process for preparing pentachloro-3-butenoic acid esters.

SUMMARY OF THE INVENTION

It is, therefore, an object of the present invention to provide a process which overcomes these drawbacks and enables preparation of pentachloro-3-butenoic acid esters in a simple manner with satisfactory conversion (80% of theory).

Upon further study of the specification and appended claims, further objects and advantages of this invention will become apparent to those skilled in the art.

These objects have been attained by providing a process which comprises treating the products of the reaction between 1-alkoxypentachloro-1,3-butadienes and chlorine with an aqueous alkali carbonate solution, optionally in the presence of a solvent and, optionally in the presence of additional diluents.

Accordingly, from the products (II) of the reaction of 1-alkoxypentachloro-1,3-butadienes (I) with chlorine is possible to directly prepare the pentachloro-3-butenoic acid esters (IV), without having to pass through the intermediate product of pentachloro-3-butenoic acid chloride (III) as illustrated below:

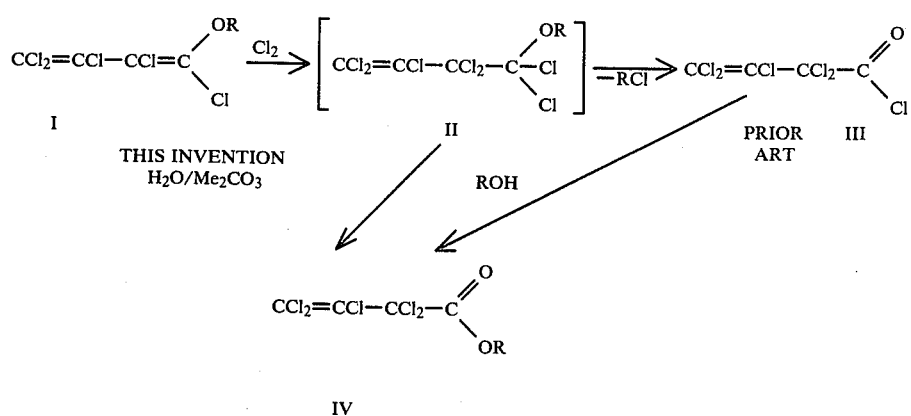

DETAILED DISCUSSION

It could not be foreseen that, in the reaction of this invention, the chlorine atoms in the 1-position are almost exclusively saponified, whereas the chlorine atoms in the 2-position remain in the molecule. It also could not be foreseen that an aqueous solution of alkali metal carbonates is exclusively capable of this selective hydrolysis, while classical saponifying agents, such as acids, for example, do not provide the desired results.

It was likewise unexpected that, in the process of this invention, the 1-alkoxypentachloro-1,3-butadienes could be used in high dilution, without a reduction in the yield of product pentachloro-3-butenoic acid esters, whereas in the process proceeding via the pentachloro-3-butenoic acid chloride, a further concentration to more than 80% by weight is required, since otherwise the yield drops drastically (see Comparative Examples A and B).

In summation, the primary advantages of the process of this invention thus reside, in that, by the direct conversion of the chlorination product (II) into the pentachlorobutenoic acid ester (IV), one less reaction stage is required than in the process of the prior art which proceeds via (III). As a result, there is an additional savings in chemical agents since the alkoxy group remains in the molecule and need not be reintroduced. Furthermore, no increased concentration of 1-alkoxypentachloro-1,3-butadiene, obtained during its production process in a concentration of about 20-60% by weight (after elimination of the alcohol), is necessary. This is an especially significant factor in view of the instability of this compound under heating, especially in the presence of iron-containing vessel materials.

1-Alkoxypentachloro-1,3-butadienes particularly suitable for the reaction to the pentachlorovinylacetic acid ester include those, the alkyl residues of which contain 1-8, especially 2-4 carbon atoms. The concentration of 1-alkoxypentachloro-1,3-butadiene in the reaction charge is to be at least 15% by weight and generally up to 100% by weight. Preferably, there are utilized the raw materials obtained in the preparation reaction of hexachloro-1,3-butadiene with alkali metal alcoholates or with alkali metal hydroxides in alcoholic solution, after elimination of the excess alcohol. These have a content of 20-60% by weight of 1-alkoxypentachloro-1,3-butadiene.

The amount of chlorine required for the reaction with the 1-alkoxypentachloro-1,3-butadienes (1) is 1.0-1.6 moles preferably 1.2-1.4 moles, per mole of 1-alkoxypentachloro-1,3-butadiene. Advantageously, gaseous chlorine is introduced into the reaction charge until saturation occurs. The reaction temperature for the reaction of I with chlorine is generally 5°-40° C., preferably 15°-30° C. and the reaction time generally is 15 minutes-10 hours, preferably 20 minutes-4 hours. Pressure is generally atmospheric. Excess pressure may be employed.

In the treatment of the chlorination products (II) with the aqueous alkali metal carbonate solution, the amounts of alkali metal carbonate, preferably sodium carbonate or potassium carbonate, as well as the amounts of water can be varied within wide limits. The amount of aqueous alkali metal carbonate solution, however, should be measured so that at least 2 moles of water are present (up to, e.g. 20 moles) per 1 mole of 1-alkoxypentachloro-1,3-butadiene, and 0.8-2.5 moles, preferably 1.0-2.0 moles of alkali metal carbonate are present per mole of chlorine reacted with II. Per mole of actual reactant, 1-alkoxyheptachloro-3-butene, 2-20 moles of water and 0.8-2.5 moles of alkali metal carbonate should be used.

It is advantageous to conduct this reaction in the presence of a solvent, especially an alcohol but also possibilities include ethers and/or ketons which are capable to solve organic materials as well as miscible with water, for example dioxane, tetrahydrofuran and acetone.

Preferably, the solvent is the alkanol which corresponds to the alkoxy group in the 1-alkoxpentachloro-1,3-butadiene. In case of alcohols, such as n-butanol, which have limited miscibility with water, preferably, a quantity of alcohol is employed so that there will be no formation of a second liquid phase. The reaction temperature for the treatment of II with the aqueous alkali metal carbonate solution is generally 60°-105° C., preferably 80°-90° C., the time of reaction is generally 0.5-10 hours, preferably 1-3 hours, and in general, vigorous agitation is employed. This temperature—insofar as the process is conducted without excess pressure—can be limited at the upper end by the boiling point of the alcohol employed. Normal atmospheric pressure is preferred but an excess pressure (and if desired, the corresponding higher temperatures which are possible thereby) can be used.

The mentioned diluents refer in general to the higher boiling by-products and unreacted hexachloro-1,3-butadiene obtained in the described preparation of the starting material 1-alkoxypentachloro-1,3-butadienes from hexachloro-1,3-butadiene.

Unless noted otherwise herein, the conditions for the reaction of the 1-alkoxypentachloro-1,3-butadiene with chlorine are fully conventional, e.g., the reaction is conducted with the exclusion of light. In general, the inventive step of this reaction is carried out separately from the preceding conventional chlorine reaction, e.g., after the chlorine has been purged from the reaction medium.

The pentachloro-3-butenoic acid esters prepared by the process of this invention can be activating cocatalysts in the production of ethylene-α-olefin and ethylene-α-olefindiene copolymers with the aid of so-called Ziegler-Natta catalysts, preferably those based on vanadium compounds soluble in organic solvents and ethyl aluminum sesquichloride.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsover. In the following example(s), all temperatures are set forth uncorrected in degrees Celsius; unless otherwise indicated, all parts and percentages are by weight.

The analyses by gas chromatography were conducted on a column packed with the silicone rubber UCCW 982.

EXAMPLE 1

With the exclusion of light, 14.7 g (0.207 mole) of dry chlorine was introduced within ½ hour into 57.2 g of 98% by weight of 1-ethoxypentachloro-1,3-butadiene (=0.188 mole); the temperature was maintained at 20°-26° C. with external cooling. The 2.6 g of chlorine condensed in the subsequently connected cooling trap was reintroduced, the reaction mixture absorbing approximately 1.8 g. The reaction mixture was allowed to stand for 2 hours; then the dissolved chlorine was degasified with a gentle nitrogen stream. In this way, 70.0 g of reaction mixture was obtained. This quantity was heated to 80° C. together with 150 cc of ethanol, 100 cc of water, and 20.0 g of $Na_2CO_3$ (0.189 mole). Under vigorous agitation the two-phase mixture was heated to boiling under reflux for 1 hour. After cooling, the lower phase (47.7 g) was separated from the upper phase (259.1 g) containing the ethanol, water, NaCl and $Na_2CO_3$. The content of chloride ions in the upper phase was 14.2 g (0.40 mole). After the ethanol was distilled off, an organic phase (8.4 g) was additionally separated. During the extraction of the aqueous phase with diethyl ether and subsequent evaporation of the diethyl ether, another 1.4 g was obtained. The combined organic phases (57.5 g) contained 77.4% by weight, i.e., 44.5 of pentachloro-3-butenoic acid ethyl ester; yield: 83% of theory.

EXAMPLE 2

With the exclusion of light and with external cooling, 30.7 g of chlorine was introduced at 15°–28° C. within 2¼ hours into 129.7 g of a mixture consisting of 42.3% by weight of hexachloro-1,3-butadiene, 46.5% by weight of 1-n-butoxypentachloro-1,3-butadiene (0.20 mole) and 11.2% by weight of unidentified by-products. The reaction mixture was allowed to stand for 2 hours; then the dissolved chlorine was degasified with a gentle nitrogen stream. The chemically bound amount of chlorine was 20.3 g (0.286 mole). The thus-obtained 150.0 g of reaction mixture was heated for 2½ hours to 90° C. under vigorous agitation together with 300 g of n-butanol, 30 g of water, and 21.4 g (0.20 mole) of $Na_2CO_3$. After cooling, 200 g of water was stirred into the reaction mixture. The aqueous (bottom) phase was separated; it contained 16.1 g (0.45 mole) of chloride ions. After distilling off the n-butanol from the organic (top) phase, 123.3 g was obtained, containing 38.2% by weight of hexachloro-1,3-butadiene and 45.8% by weight, i.e., 56.5 g of pentachloro-3-butenoic acid n-butyl ester. The yield was 88.9% of theory.

EXAMPLE 3

With the exclusion of light and with external cooling, 31.1 g of chlorine was introduced within 2½ hours at 15°–25° C. into 131.2 g of a mixture consisting of 42.3% by weight of hexachloro-1,3-butadiene, 46.5% by weight of 1-n-butoxypentachloro-1,3-butadiene (0.204 mole), and 11.2% by weight of unidentified by-products. The reaction mixture was first allowed to stand for 2 hours; then the dissolved chlorine was degasified with a gentle stream of nitrogen. The chemically bound quantity of chlorine was 18.8 g (0.26 mole). The reaction mixture was heated to 90° C. under vigorous agitation for 2¼ hours together with 300 g of n-butanol, 30 g of water, and 55.9 g (0.527 mole) of $Na_2CO_3$. After cooling, 400 g of water was stirred into the reaction mixture and the aqueous (bottom) phase was separated. This bottom phase contained 15.6 g (0.44 mole) of chloride ions. After removing the n-butanol by distillation from the organic (top) phase, 123.9 g of a mixture was obtained which contained 39.3% by weight of hexachloro-1,3-butadiene and 46.0% by weight, i.e., 57.0 g of pentachloro-3-butenoic acid n-butyl ester. The yield was 88% of theory.

EXAMPLE 4

With the exclusion of light and with external cooling, 124.3 g of chlorine was introduced within 2½ hours at 15°–25° C. into 605.3 g of a mixture consisting of 37.1% by weight of hexachloro-1,3-butadiene, 49.3% by weight of 1-n-butoxypentachloro-1,3-butadiene (1.0 mole), and 13.6% by weight of unidentified by-products. The reaction mixture was first allowed to stand for 2 hours; then the dissolved chlorine was degasified with a gentle nitrogen stream. The chemically bound quantity of chlorine was 89.0 g (1.25 mole). The reaction mixture (691.6 g) was heated under vigorous agitation for 2¼ hours to 90° C. together with 1,383.0 g of n-butanol, 138.3 g of water and 137.0 g (1.29 mole) of $Na_2CO_3$. After cooling, 400 g of water was stirred into the reaction mixture, and the aqueous (bottom) phase was separated; this phase contained 73.3 g (2.07 mole) of chloride ions. The brown-colored organic (top) phase was heated under reflux to boiling with 70 g of activated carbon for 1 hour; the activated carbon was removed by vacuum-filtering after cooling, and the n-butanol was distilled off from the yellowish filtrate. The distillate (1,349 g) consisted of 95.5% by weight of n-butanol and 4.4% by weight of hexachloro-1,3-butadiene; the distillation residue (507.5 g) consisted of 33.7% by weight of hexachloro-1,3-butadiene and 55.4% by weight i.e., 281.2 g of pentachloro-3-butenoic acid n-butyl ester. The yield was 89.4% of theory.

EXAMPLE 5

With the exclusion of light and with external cooling, 113.5 g of chlorine was introduced within 2¾ hours at 15°–25° C. into 537.7 g of a mixture consisting of 41.0% by weight of hexachloro-1,3-butadiene, 44.4% by weight of 1-n-butoxypentachloro-1,3-butadiene (0.80 mole) and 14.6% by weight of unidentified by-products. The reaction mixture was first allowed to stand for 2 hours; then the dissolved chlorine was degasified with a gentle nitrogen stream. The chemically bound amount of chlorine was 78.7 g (1.11 mole). The reaction mixture was heated to 90° C. for 2½ hours under vigorous agitation together with 1,232.8 g of n-butanol, 123.3 g of water and 176.5 g (1.665 mole) of $Na_2CO_3$. The liquid phase remained homogeneous. After cooling, 2,000 g of water was stirred into the reaction mixture. The aqueous (lower) phase was separated; this phase contained 65.2 g (1.84 mole) of chloride ions. The organic, brown-colored (top) phase (1,903 g) was heated to boiling under reflux for 1 hour with 100 g of activated carbon; after cooling, the activated carbon was removed by vacuum-filtering and the n-butanol was distilled off from the yellowish filtrate. The distillate (1,557 g) consisted of 98.5% by weight of butanol and 1.5% by weight of hexachloro-1,3-butadiene; the distillation residue (465 g) consisted of 35% by weight of hexachloro-1,3-butadiene and 53.2% by weight of pentachloro-3-butenoic acid n-butyl ester (=247.4 g), i.e. 98.4% of theory. In a frictional distillation over a small column, 7.8 g of the ester was recovered in the first fraction, containing primarily hexachloro-1,3-butadiene (concentration: 88.0% by weight); 21.1 g of the ester was recovered in the intermediate fraction; 186.5 g was recovered in the main fraction (concentration of the ester: 90.0% by weight); and 4.8 g was recovered in the last fraction, the total being 220.2 g. The yield after distillation was accordingly 87.5% of theory.

EXAMPLE 6

With the exclusion of light and with external cooling, 9.2 g of chlorine was introduced at 19°–28° C. within 1½ hours into 62.9 g of a mixture containing 27.4 g of 1-n-butoxy- pentachloro-1,3-butadiene (0.09 mole), 25.4 g of hexachloro-1,3-butadiene and 10.1 g of unidentified by-products. The reaction mixture was first allowed to stand for 2 hours; then the dissolved chlorine was degasified with a gentle nitrogen stream. The quantity of chemically bound chlorine was 7.1 g (0.1 mole). The reaction product (70.0 g) was heated under vigorous agitation for 2 hours to 80° C. together with 121.5 g of n-butanol, 45 g of water, 9.8 g of $Na_2CO_3$ (0.092 mole). The aqueous (bottom) phase, containing 0.161 mole of chloride ions, was separated. After distilling the butanol off from the organic (top) phase, a mixture was obtained containing, in addition to 1.4 g of 1-butoxypentachloro-1,3-butadiene, 21.8 g of pentachloro-3-butenoic acid n-butyl ester. The conversion was 95%; the selectivity was 80% of theory.

COMPARATIVE EXAMPLE A

With the exclusion of light and with external cooling, 22 g of chlorine was introduced within 1 hour at 15°–30° C. into 225.6 g of a mixture consisting of 39.2% by weight of hexachloro-1,3-butadiene, 44.7% by weight of 1-ethoxy- pentachloro-1,3-butadiene (0.377 mole) and 16.1% by weight of unidentified by-products; 19.4 g of the chlorine was absorbed. Of the thus-obtained 255.3 g reaction product, 130.0 g was heated gradually to 200° C. and left for 2.5 hours at this temperature. The distillation of the reaction mixture resulted in 96.0 g of a distillate containing 37.8% by weight of pentachloro-3-butenoic acid chloride, i.e., a yield of 70% of theory.

COMPARATIVE EXAMPLE B

With the exclusion of light and with external cooling, 20 g of chlorine was introduced within 1 hour at 20°–25° C. into 132.1 g of a mixture consisting of 36.3% by weight hexachloro-1,3-butadiene, 53.0% by weight (0.235 mole) of 1-n-butoxypentachloro-1,3-butadiene and 10.7% by weight of unidentified by-products; 19.4 g of the chlorine was absorbed. The reaction mixture was then gradually heated to 200° C. and left for 7 hours at this temperature. The distillation of the reaction charge resulted in 91.2 g of a distillate containing 39.1% by weight of pentachloro-3-butenoic acid chloride, i.e. a yield of 62% of theory.

The preceding example(s) can be repeated with similar success by substituting the generically or specifically described reactants and/or operating conditions of this invention for those used in the preceding example(s).

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for preparing a pentachloro-3-butenoic acid alkyl ester which comprises reacting the corresponding 1-alkoxyheptachloro-3-butene with an aqueous solution of an alkali metal carbonate.

2. The process of claim 1 which is conducted in the presence of a solvent miscible with water and in which the organic compounds present in the reaction mixture are soluble.

3. The process of claim 1 wherein the starting material 1-alkoxyheptachloro-3-butene is the solution obtained as the reaction product of the reaction of the corresponding 1-alkoxypentachloro-1,3-butadiene with chlorine.

4. The process of claim 2, wherein an alcohol is the solvent.

5. The process of claim 4 wherein the alcohol solvent is the alkanol corresponding to the alkoxy group of the 1-alkoxyheptachloro-3-butene.

6. The process of claim 1 wherein the reaction temperature is 60°–105° C.

7. The process of claim 3 which is conducted in the presence of a diluent which comprises the unreacted hexachloro-1,3-butadiene and high boiling by-products which are present in said reaction product solution in addition to the 1-alkoxyheptachloro-3-butene.

8. The process of claim 3 wherein the reaction with the aqueous carbonate solution is conducted in the presence of an alcohol solvent.

9. The process of claim 8 wherein the alcohol solvent is the alcohol corresponding to the alkoxy group in the 1-alkoxypentachloro-1,3-butadiene.

10. The process of claim 1 for preparing a pentachloro-3-butenoic acid alkyl ester which comprises reacting the corresponding 1-alkoxypentachloro-1,3-butadiene with chlorine and reacting the resultant reaction products which include the corresponding 1-alkoxyheptachloro-3-butene with an aqueous solution of an alkali metal carbonate.

11. The process of claim 1, 3 or 10 wherein per mole of 1-alkoxyheptachloro-3-butene, 2–20 moles of water and 0.8–2.5 moles of alkali metal carbonate are used.

* * * * *